US005543042A

United States Patent [19]

Filan et al.

[11] Patent Number: 5,543,042
[45] Date of Patent: Aug. 6, 1996

[54] WASTE AGENT RESERVOIR FOR SUCTION DRAINAGE SYSTEM

[75] Inventors: Finbarr J. Filan, Sligo; Pascal J. Maher, Donegal; Christian Shaw, Kilkenny, all of Ireland

[73] Assignee: Abbott Laboratories, Abbott Park, Ill.

[21] Appl. No.: 413,569

[22] Filed: Mar. 30, 1995

[51] Int. Cl.$^6$ ........................................................ C02F 1/68
[52] U.S. Cl. ........................ 210/198.1; 210/251; 210/466
[58] Field of Search ................................ 210/198.1, 209, 210/251, 282, 466–468, 474, 476

[56] References Cited

U.S. PATENT DOCUMENTS

| | | | |
|---|---|---|---|
| 4,024,991 | 5/1977 | Tyson et al. | 210/466 |
| 4,145,291 | 3/1979 | Console et al. | 210/466 |
| 5,139,666 | 8/1992 | Charbonneau et al. | 210/466 |
| 5,200,070 | 4/1993 | McMenamin | 210/474 |
| 5,240,620 | 8/1993 | Shalev | 210/474 |
| 5,405,526 | 4/1995 | Sutera | 210/474 |
| 5,417,860 | 5/1995 | Kay | 210/474 |

*Primary Examiner*—Thomas G. Wyse
*Attorney, Agent, or Firm*—A. Nicholas Trausch

[57] ABSTRACT

The present invention is directed to a waste treating reservoir for treating waste collected using an associated suction system. A disposable receptacle connected to an associated suction system includes a sealed chamber such as a liner and a lid with a pour spout. The waste treating reservoir includes a closed container with an open mouth for storing a waste treating agent. A cylindrical wall forms a diffuser cap and has an open end portion and a substantially closed end portion. The closed end portion has a plurality of apertures opening radially through the cylindrical wall. The open end portion of the cylindrical diffuser cap fits telescopically over the open mouth of the agent container. The reservoir system further includes a double-walled sleeve having an inner wall and a generally concentric outer wall for attaching the combined diffuser cap and agent container to the spout of the disposable receptacle lid. The inside surface of the inner wall of the sleeve sealingly covers the radially opening apertures in the diffuser cap when the cap is in a first position relative to the sleeve. The outside surface of the inner wall and the outer wall are engagable with the cover spout of the receptacle so that the diffuser cap is slidable to a second position in the double-walled sleeve. At the second position, the radial opening apertures are moved axially beyond the inside surface of the inner wall of the sleeve. This allows an open passageway for the waste treating agent to flow from the interior of the agent reservoir to the chamber of the disposable receptacle. The waste treating reservoir of the present invention is configured so the system can be set up prior to the surgical procedure and can be readily activated immediately after the surgical procedure so that hazardous waste can be treated promptly and efficiently.

7 Claims, 3 Drawing Sheets

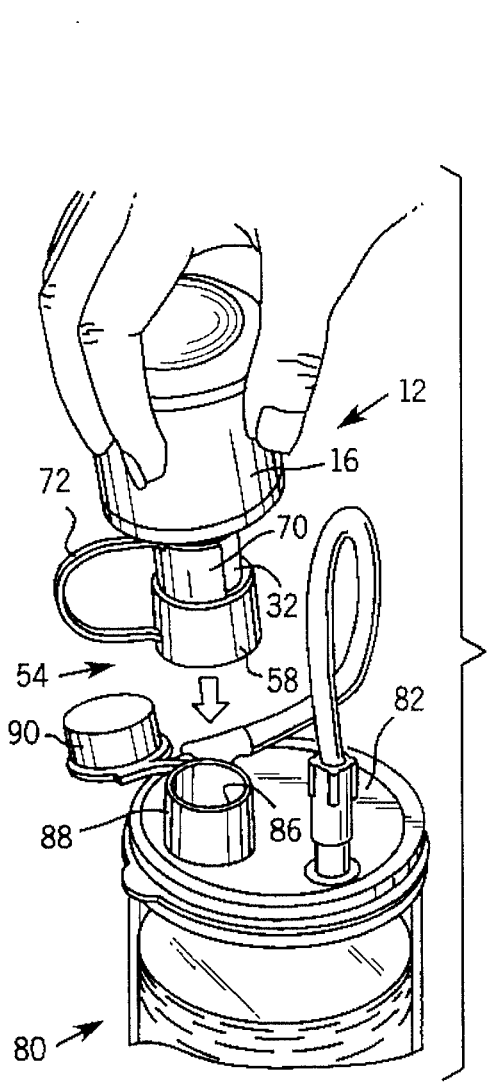
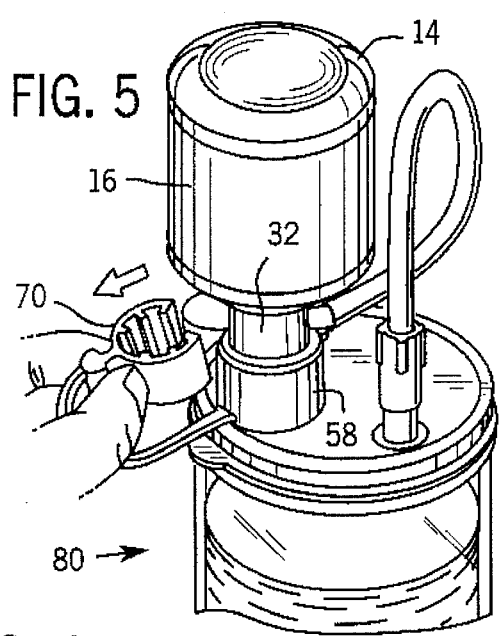
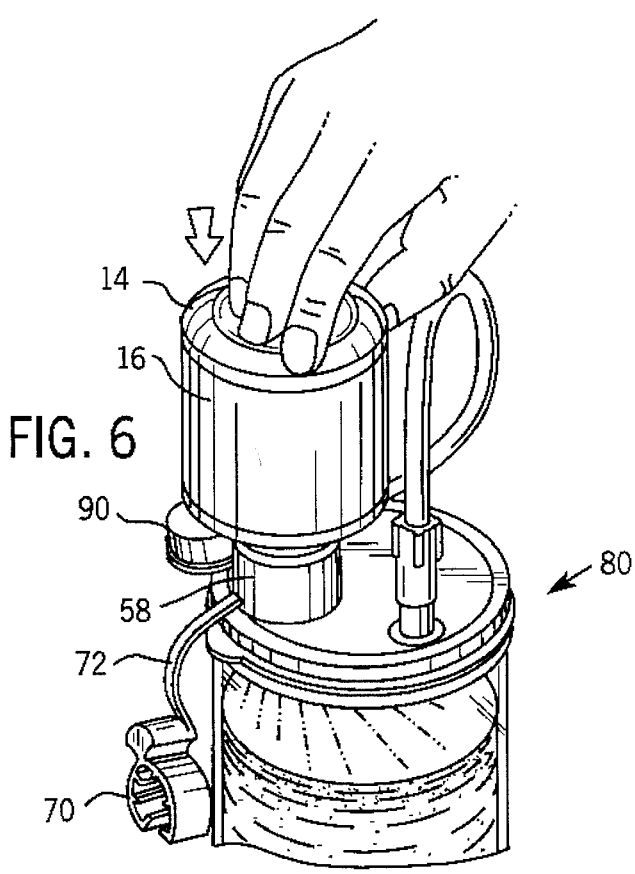

5,543,042

WASTE AGENT RESERVOIR FOR SUCTION DRAINAGE SYSTEM

FIELD OF THE INVENTION

The present invention relates generally to a reservoir containing a waste treating agent for use with a disposable waste receptacle used with an associated suction drainage system and more specifically, to a reservoir that can be positioned on a disposable waste receptacle to treat waste collected using the associated suction drainage system so that the reservoir can be prepositioned before and activated after the suction drainage procedure.

BACKGROUND OF THE INVENTION

Suction drainage systems in use today typically have a disposable receptacle such as a rigid container or a flexible liner that collects waste (i.e., bodily fluids) from surgical and other patient procedures. A fluid connection line connects the disposable receptacle to the body of the patient. Another line connects the receptacle to a suction source. The aspirated waste is often highly infectious and any exposure caused by spills or leaks of the receptacle should be avoided. Spills and leaks are most common during transportation or changing of receptacles.

Therefore, it is desirable to provide an absorbent, a gelling agent, or a germicide to treat the waste before disposal to reduce the possibility of exposure. In some known waste-treating systems, the reservoir containing the waste treating agent is permanently and/or integrally attached to the disposable receptacle of the suction drainage system. A permanent reservoir limits the ability to use different waste treating agents in different situations. Alternatively, a flexible attachment system is disclosed in U.S. patent application Ser. No. 269,496, entitled, "GELLING TREATMENT FOR SUCTION DRAINAGE", and assigned to and sold by Abbott Laboratories, the assignee of the present invention. One limitation of the above-disclosed flexible attachment waste treatment system is that the system cannot be set up prior to the suction drainage procedure of the waste fluid. Thus, a surgical assistant is required to set up and activate the waste treating system while the surgical procedure is under way or after the surgical procedure has been completed. A small surgical team may not have the extra personnel to initiate this waste treating during or immediately after the surgical procedure. Thus, the hazardous fluids may be left untreated and pose a potential danger until well after the surgical procedure is completed.

The present waste treating system has been particularly configured to facilitate prompt, efficient, and convenient treatment of waste solutions during or after the surgical procedure. The reservoir containing the waste treating agent can be placed in position to treat the waste prior to the start of the surgery, and then readily activated when a disposable receptacle reaches capacity. Thus, the waste containing receptacle can be treated immediately after reaching capacity and therefore reduces the potential for contamination.

SUMMARY OF THE INVENTION

The present invention is directed to a waste treating reservoir for treating waste collected using an associated suction system. A disposable receptacle connected to an associated suction system includes a sealed chamber such as a liner and a lid with a pour spout. The waste treating reservoir includes a closed container with an open mouth for storing a waste treating agent. A cylindrical wall forms a diffuser cap and has an open end portion and a substantially closed end portion. The closed end portion has a plurality of apertures opening radially through the cylindrical wall. The open end portion of the cylindrical diffuser cap fits telescopically over the open mouth of the agent container. The reservoir system further includes a double-walled sleeve having an inner wall and a generally concentric outer wall for attaching the combined diffuser cap and agent container to the spout of the disposable receptacle lid. The inside surface of the inner wall of the sleeve sealingly covers the radially opening apertures in the diffuser cap when the cap is in a first position relative to the sleeve. The outside surface of the inner wall and the outer wall are engagable with the cover spout of the receptacle so that the diffuser cap is slidable to a second position in the double-walled sleeve. At the second position, the radial opening apertures are moved axially beyond the inside surface of the inner wall of the sleeve. This allows an open passageway for the waste treating agent to flow from the interior of the agent reservoir to the chamber of the disposable receptacle. The waste treating reservoir of the present invention is configured so the system can be set up prior to the surgical procedure and can be readily activated immediately after the surgical procedure so that hazardous waste can be treated promptly and efficiently.

Other features and advantages of the present system will become readily apparent from the following detailed description, the accompanying drawings, and the appended claims.

BRIEF DESCRIPTION OF THE DRAWINGS

FIG. 4 is a perspective view of the assembled reservoir system and the disposable receptacle immediately prior to set-up and connection;

FIG. 5 is a perspective view of the reservoir system in the ready position on the receptacle with the safety dip being removed; and FIG. 6 is a perspective view of the reservoir system after the system has been activated to treat the waste.

DETAILED DESCRIPTION OF THE INVENTION

Figure 1:
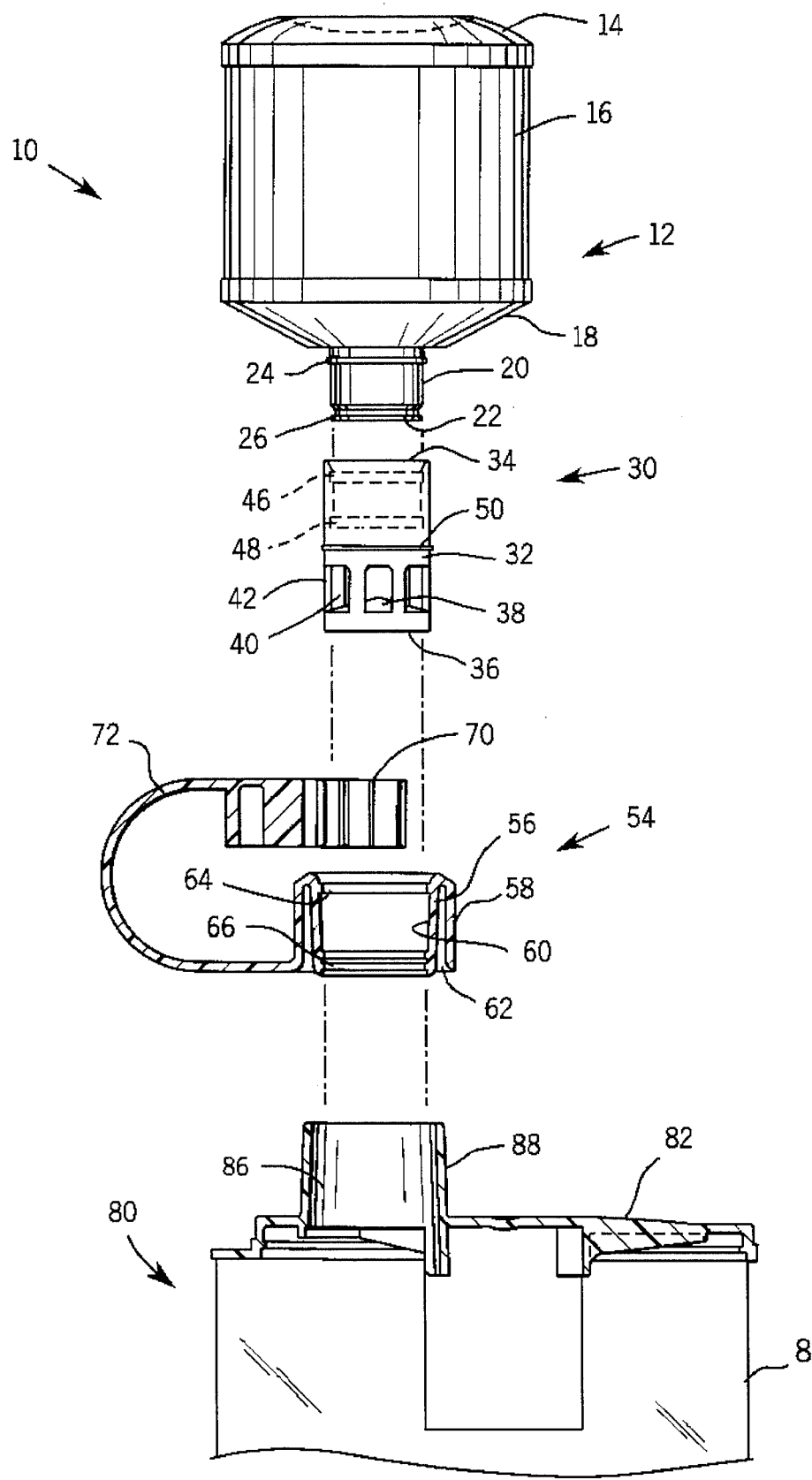
FIG. 1 is an exploded partial cross-sectional view of the components of the waste agent reservoir system of the present invention and the lid of a disposable receptacle.
Figure 2:
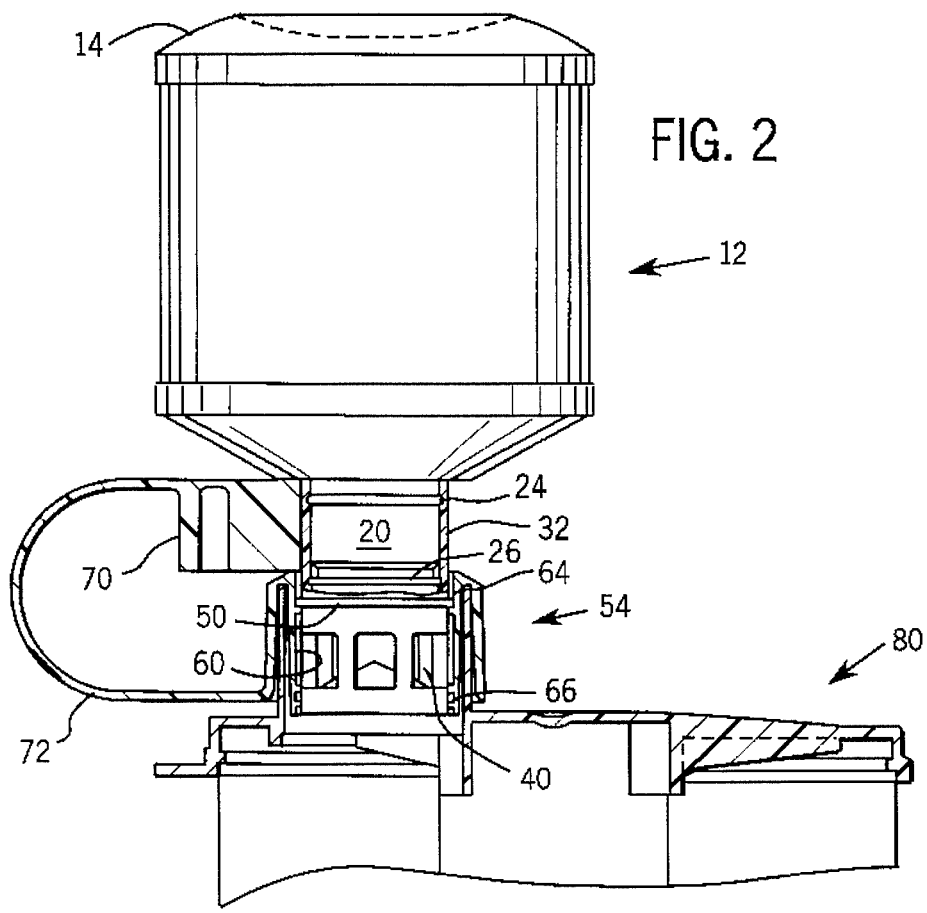
FIG. 2 is a partial cross-sectional view of the reservoir system in a ready position on the lid of the receptacle.

While the present invention is susceptible of embodiment in various forms, there will be shown in the drawings and will hereinafter be described a presently preferred embodiment, with the understanding that the present disclosure is to be considered an exemplification of the invention and is not intended to limit the invention to the specific embodiment illustrated.

With reference now to FIG. 1, therein is illustrated an exploded view of a waste treating reservoir system 10 embodying the principles of the present invention. The system includes a substantially closed container 12 including an integral bottom 14, sidewall 16, and shoulder 18. A cylindrical neck portion 20 extends from the shoulder and includes an open mouth 22. A first outside circumferential lip 24 and a second parallel outside circumferential lip 26 are positioned on the neck portion. The container 12 may be blow-molded from a suitable thermoplastic such as a high density polyethylene (HPD).

The diffuser cap 30 includes a cylindrical wall portion 32 having an open end 34 and a substantially closed end 36. The closed end is defined by an integral conical end wall 38 having an apex pointed toward the open end of the diffuser cap. A plurality of apertures 40 open radially through the lower one half of the cylindrical sidewall of the diffuser cap to provide passageways from the interior of the diffuser cap. The cylindrical sidewall may be reinforced between the apertures by internal longitudinal ribs 42. The ribs may also function as guides for guiding waste treating material down the conical end wall surface through an appropriate aperture.

The diffuser cap 30 also includes a first inside circumferential groove 46 at the open end of the diffuser cap and a second inside circumferential groove 48 in the middle of the diffuser cap. A slightly raised outside circumferential lip 50 is positioned on the outside surface of the diffuser cylindrical wall. The diffuser cap is preterably injection-molded of a thermoplastic such as polypropylene.

The first and second inside circumferential grooves 46 and 48 of the diffuser cap mate with the first and second outside circumferential lips 24 and 26 on the neck portion of the container 12 when the diffuser cap is telescopically mated onto the neck portion of the container. The lips and grooves are constructed so that the diffuser cap 30 and container 12 can be easily slip-fit together during assembly of the reservoir system, but strongly resist separation of the cap and container.

A double-walled sleeve 54 is also injection molded of a suitable thermoplastic such as HPD as a third component of the waste treating reservoir system. The double-walled sleeve includes a inner wall 56 and an outer wall 58. While the two walls are substantially concentering, preferably at least one of the walls has a slight angle to the axis of the sleeve so as to provide a snug tapering fit to matingly seal with the cylindrical flange.

The inside surface 60 of the inner wall also sealingly covers the openings 40 in the diffuser cap when the cap is in a first position relative to the sleeve. The inside surface of the sleeve has a shallow upper inside surface groove 64 and a shallow lower inside surface groove 66. The first position of the diffuser cap relative to the sleeve is defined when the slightly raised outside circumferential lip 50 of the diffuser cap is in the shallow upper inside surface groove 64 of the sleeve. The double-walled sleeve also includes an open channel 62 between the inner and outer wall. The inner wall 56 and the outer wall 58 are constructed so that the open channel telescopically fits over the extending cylindrical flange portion 88 of the pour spout on the receptacle lid.

The double-walled sleeve 54 also includes a safety clip 70 that is integrally connected to the sleeve by a tether connection 72. The clip is C-shaped so that the ends of the clip extend slightly beyond that of a semi-circle. The inside diameter of the clip semi-circle is equal in size to the outside diameter of the diffuser cap 30 so that the arms of the plastic clip will resiliently engage around the diffuser. The axial length of the clip 70 is equal to the axial length of the upper half of the diffuser cap, i.e., from the raised outside lip 50 to the closed end 36. When the clip is engaged around the diffuser cap, the axial length of the clip ensures that the plurality of open apertures 40 in the diffuser cap remain covered by the inside surface 60 of the inner wall of the double-walled sleeve.

The disposable receptacle 80 includes a hard lid B2 and a flexible liner 84 that is sealed to and depends from the lid. The liner and lid together define a sealed chamber having, for example, a one, two or three liter capacity. The receptacle holds the fluid waste aspirated by the suction drainage system. The lid includes a pour spout 86 that is defined by a cylindrical flange 88 and sealed by a removable cap 90. The cylindrical flange may also be tapered for a tapering fit between inner wall 56 and outer wall 58 of the double-walled sleeve. The channel 62 between the inner and outer wall of the double-walled sleeve is orientated so that the open end of the channel is directed away from the container 12. The channel allows the waste agent reservoir system to be easily and sealingly slipped into place on the pour spout of the receptacle.

Figure 3:
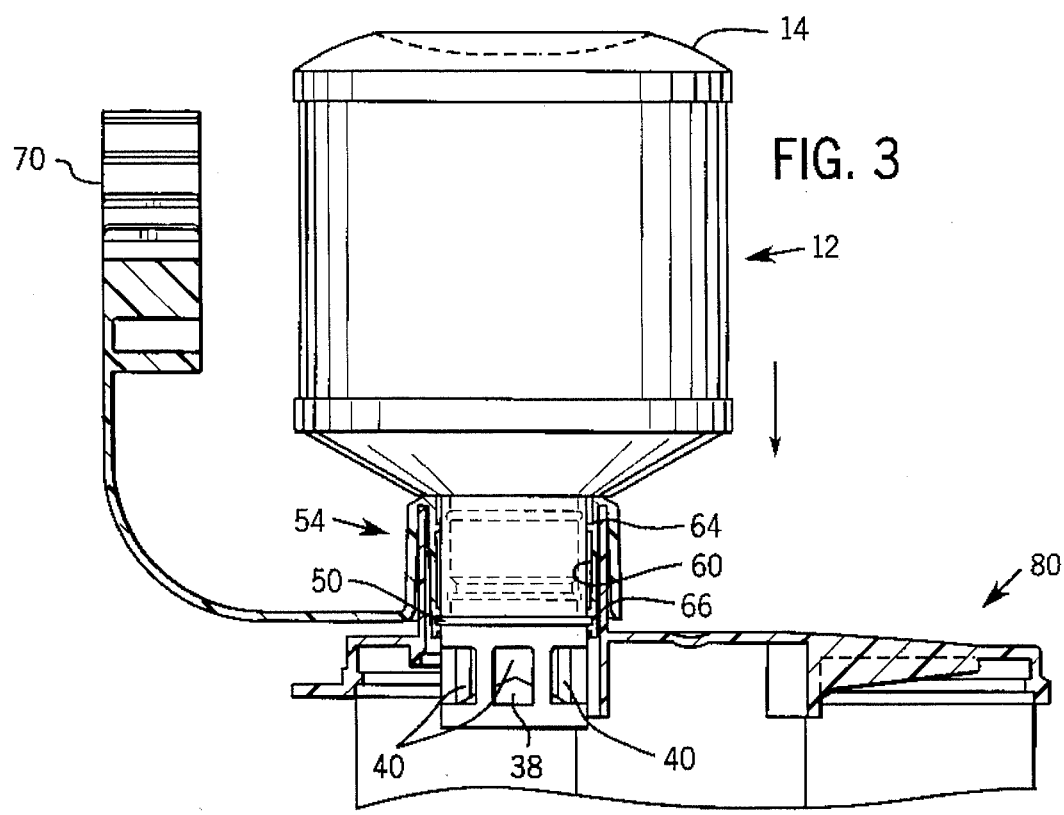
FIG. 3 is a partial cross-sectional view of the reservoir system in an activated position on the lid of the receptacle so as to treat the waste in the receptacle.

Use of the present invention for treating waste collected in a disposable receptacle by a suction drainage system will now be described. With reference to FIG. 4, the assembled waste agent reservoir system 10 is orientated so that the open channel of the double-walled sleeve 54 faces the cylindrical flange 88 of the pour spout 86. The waste agent reservoir 10 is connected to the disposable lid and liner of the receptacle with the safety clip 70 in place on the upper half of the diffuser so as to prevent premature or accidental activation of the system. With the waste agent reservoir 10 firmly in position (FIG. 5), the clip 70 is removed from the diffuser cap. As seen with reference to FIGS. 3 and 6, a gentle push on the bottom 14 of the reservoir container will slide the diffuser cap to a second position in the double-walled sleeve. The second position is defined so that the slightly raised outside circumferential lip 50 of the diffuser cap moves from the shallow upper inside surface groove 64 to the shallow lower inside surface groove 66 of the double-walled sleeve. The result of this movement, shown in FIG. 3, causes the plurality of open apertures 40 in the diffuser cap to move beyond the inside surface 60 of the inner wall of the double-walled sleeve 54. In the second position, a passageway for the waste treating agent that is in the reservoir 10 is opened from the interior of the container 12 to the receptacle chamber. Furthermore, the conical end wall 38 of the diffuser cap disperses the waste treating agent throughout the fluid waste as the agent drops into the chamber. This dispersion promotes faster and more effective waste treatment, whether the agent be a gelling, solidifying, disinfecting, or any combination of the above.

The double-walled sleeve 54 and the end wall 38 of the diffuser cap can sealingly replace the spout cap 90 on the pour spout so that the waste agent reservoir system can be prepositioned on the disposable receptacle before the surgical procedure begins. The sealing provided by the sleeve and end wall allow the suction drainage system to operate and collect the waste in the liner with the waste agent reservoir prepositioned in place. Thus, when a disposable receptacle is at capacity, a surgical assistant can quickly remove the safety clip 70 and push the bottom 14 of the container down to activate the system. The waste agent quickly and timely acts on the potentially hazardous waste fluid. This reduces the risk that the waste fluid will be in an untreated state when it is desired to change or move the disposable receptacles.

From the foregoing, it will be observed that numerous modifications and variations can be effected without departing from the true spirit and scope of the novel concept of the present invention. The present disclosure is to be understood broadly and no limitation with respect to the specific embodiment disclosed herein is intended or should be inferred. The disclosure is intended to cover, by the appended claims, all such modifications as fall within the scope of the claims.

What is claimed is:

1. A reservoir system for treating waste collected using an associated suction system in a disposable receptacle having a chamber and a lid with a pour spout, comprising:

a closed container with an open mouth for storing a waste-treating agent;

a cylindrical diffuser cap having an open end portion and a substantially closed end portion, the closed end portion having a plurality of radial apertures, and the open end portion telescopically mating over the open mouth of the agent container;

a double-walled sleeve having an inner wall and a generally concentric outer wall for attaching the combined diffuser cap and agent container to the cover spout of the receptacle lid, the inside surface of the inner wall sealingly covering the radial apertures in the diffuser cap when the cap is in a first position relative to the sleeve, the outside surface of the inner wall and the outer wall sealingly engaging the spout of the receptacle lid so that the diffuser cap is axially slidable to a second position in the double-walled sleeve wherein the radial apertures are beyond the inside surface of the inner wall of the sleeve so that a passageway for the waste-treating agent is open from the agent container to the receptacle chamber.

2. The reservoir of claim 1 further including means for preventing the diffuser cap from prematurely sliding from the first position to the second position in the double-walled sleeve.

3. The reservoir of claim 2 wherein the preventing means is a clip removably positioned on the open end portion of the diffuser cap.

4. The reservoir of claim 3 wherein the reservoir system is sealingly attachable to the pour spout of the receptacle lid so that the suction system may function properly.

5. The reservoir of claim 4 wherein the closed end of the diffuser cap includes a conical end wall that tapers toward the plurality of radial apertures so that the waste-treating agent is diffused from the reservoir system into the receptacle chamber when the diffuser cap is in the second position.

6. The reservoir of claim 5 further including a tether attaching the removable clip to the sleeve.

7. The reservoir of claim 5 wherein the plurality of radial apertures is evenly spaced around the cylindrical diffuser cap.

* * * * *